United States Patent
Koubi et al.

(10) Patent No.: US 9,554,872 B2
(45) Date of Patent: Jan. 31, 2017

(54) INTRAORAL DEVICE FOR AUTOMATED PREPARATION OF THE TEETH WITH A VIEW TO PERFORMING PARTIAL OR PERIPHERAL RESTORATIONS

(71) Applicants: Stephen Koubi, Marseilles (FR); Galip Gurel, Istanbul (TR)

(72) Inventors: Stephen Koubi, Marseilles (FR); Galip Gurel, Istanbul (TR)

( * ) Notice: Subject to any disclaimer, the term of this patent is extended or adjusted under 35 U.S.C. 154(b) by 2 days.

(21) Appl. No.: 14/398,810

(22) PCT Filed: Apr. 29, 2013

(86) PCT No.: PCT/FR2013/050948
§ 371 (c)(1),
(2) Date: Mar. 13, 2015

(87) PCT Pub. No.: WO2013/164537
PCT Pub. Date: Nov. 7, 2013

(65) Prior Publication Data
US 2015/0182299 A1    Jul. 2, 2015

(30) Foreign Application Priority Data
May 4, 2012 (FR) ................................ 12 54147

(51) Int. Cl.
*A61C 3/02* (2006.01)
*A61B 5/00* (2006.01)
(Continued)

(52) U.S. Cl.
CPC .............. *A61C 3/02* (2013.01); *A61B 5/0088* (2013.01); *A61B 5/1077* (2013.01); *A61B 5/682* (2013.01);
(Continued)

(58) Field of Classification Search
CPC ......... A61C 1/007; A61C 3/02; A61C 9/0046; A61C 9/004; A61C 1/082; A61C 1/0007; A61B 5/0088; A61B 5/1077; A61B 5/682; Y10S 901/41
(Continued)

(56) References Cited

U.S. PATENT DOCUMENTS

| 5,113,424 A | 5/1992 | Burdea et al. |
| 5,347,454 A * | 9/1994 | Mushabac ......... G05B 19/4207 433/214 |

(Continued)

FOREIGN PATENT DOCUMENTS

| EP | 0345975 | 12/1989 |
| FR | 2036992 | 12/1970 |
| WO | WO 94/03120 | 2/1994 |

OTHER PUBLICATIONS

Gurel G. "Predictable, precise and repeatable tooth preparation for porcelain laminate veneers in complex cases", Pract proced Aesthet Dent. 2003; 15(1) p. 17-24.

*Primary Examiner* — Nicholas Lucchesi
(74) *Attorney, Agent, or Firm* — Pearl Cohen Zedek Latzer Baratz LLP

(57) ABSTRACT

The invention relates to an intraoral device for automated preparation of the teeth with a view to performing partial or peripheral dental restoration, which includes: a splint (1) suitable for being positioned in the mouth of a patient, said splint including a means (13) for maintaining the position thereof inside said mouth; at least one mobile cutting tool (2) combined with said splint; and an electronic management unit which makes it possible to control said cutting tool, characterized in that: said cutting tool (2) is configured so as to cut at least the labial surface of the tooth (D1) to be prepared, said tool being mounted on a mobile carriage (23) moving along a rail (24) attached to the splint (1), opposite
(Continued)

the labial surface of the tooth (D1) to be prepared, said rail having a curvature that matches the dentition (D) of the patient; said splint (1) includes at least one 3D digitization tool (4) arranged such as to digitize at least the labial surface of said tooth to be prepared, said digitization tool being connected to the management unit (6) so that the digitized data can be transferred to said management unit; and said management unit is configured so as to control the movement of said cutting tool (2) in accordance with the digitized data.

11 Claims, 7 Drawing Sheets

(51) Int. Cl.
  *A61B 5/107* (2006.01)
  *A61C 1/08* (2006.01)
  *A61C 1/00* (2006.01)
  *A61C 9/00* (2006.01)

(52) U.S. Cl.
  CPC ............. *A61C 1/0007* (2013.01); *A61C 1/082* (2013.01); *A61C 9/0046* (2013.01); *A61C 9/004* (2013.01); *Y10S 901/41* (2013.01)

(58) Field of Classification Search
  USPC ...................................... 433/24, 27, 29, 215
  See application file for complete search history.

(56) References Cited

U.S. PATENT DOCUMENTS

| | | | | |
|---|---|---|---|---|
| 5,597,304 | A  * | 1/1997 | Ray | A61C 1/082 433/27 |
| 7,346,417 | B2 * | 3/2008 | Luth | A61C 13/0004 128/920 |
| 2004/0015176 | A1 | 1/2004 | Cosman | |
| 2004/0155975 | A1 | 8/2004 | Hart et al. | |
| 2005/0023781 | A1 | 2/2005 | Ortega | |
| 2006/0240378 | A1* | 10/2006 | Weinstein | A61B 5/103 433/76 |

* cited by examiner

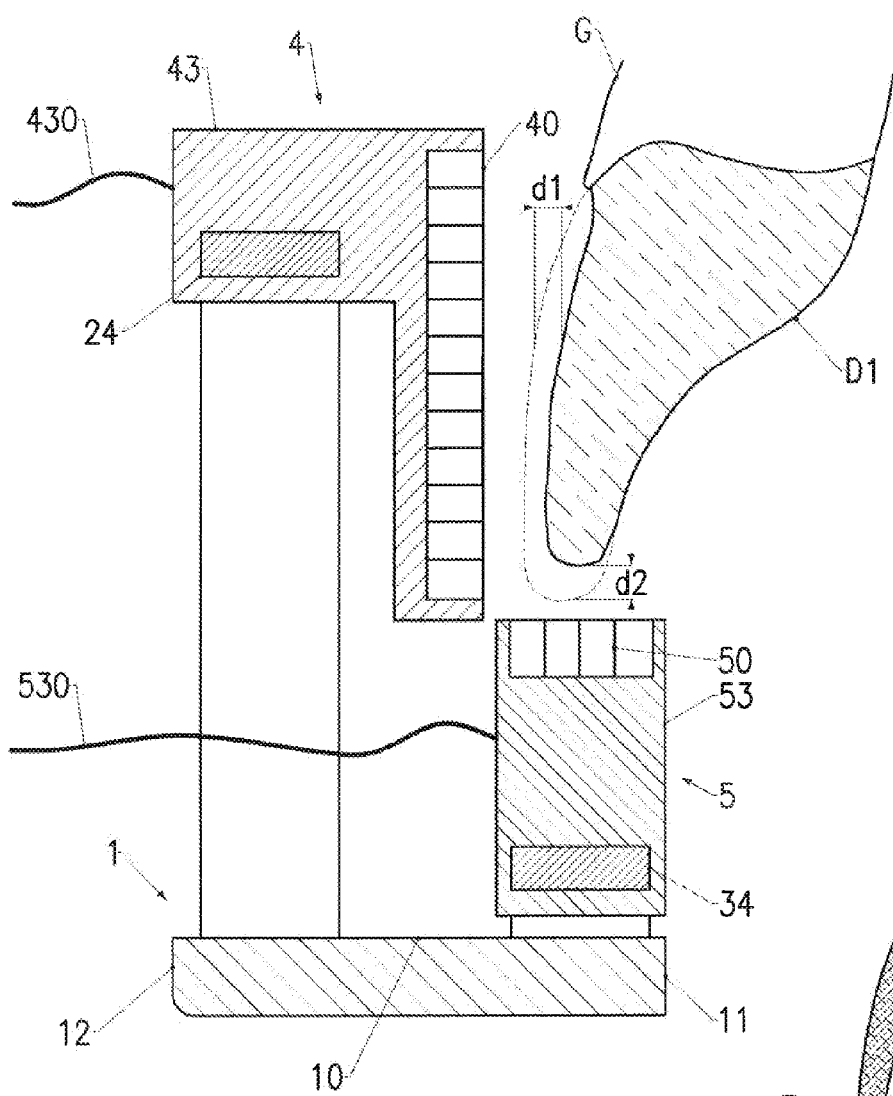
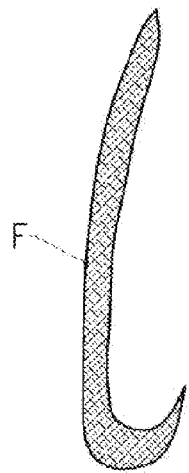
Fig. 6
Fig. 7

INTRAORAL DEVICE FOR AUTOMATED PREPARATION OF THE TEETH WITH A VIEW TO PERFORMING PARTIAL OR PERIPHERAL RESTORATIONS

CROSS-REFERENCE TO RELATED APPLICATIONS

This application is a National Phase Application of PCT International Application No. PCT/FR2013/050948, entitled "INTRAORAL DEVICE FOR AUTOMATED PREPARATION OF THE TEETH WITH A VIEW TO PERFORMING PARTIAL OR PERIPHERAL RESTORATIONS", International Filing Date Apr. 29, 2013, published on Nov. 7, 2013 as International Publication No. WO 2013/164537, which in turn claims priority from French patent Application No. 1254147, filed May 4, 2012, all of which are incorporated herein by reference in their entirety.

FIELD OF THE INVENTION

The purpose of the invention is an intraoral device for the automated preparation of the teeth for performing partial or peripheral restorations.

The invention involves dental techniques enabling the preparation of a patient's tooth for performing a facet. In addition, it involves in particular robotic dental equipment enabling automatic drilling in the mouth, without the dentist having to use the cutting tool.

BACKGROUND

A ceramic facet permits covering the labial surface of a tooth that is stained, discolored, deformed or slightly deteriorated by use. Facets are mostly placed on central incisors up to the first premolars. To prepare a tooth for placing a facet, the dentist must remove a fine layer of enamel on the labial surface of the tooth. A print of the tooth thus prepared is thus made, then transmitted to a laboratory to make the facets.

The inventor has developed a technique that permits minimizing the removed enamel layer ("GUREL G. Predictable, precise and repeatable tooth preparation for porcelain laminate veneers. Pract Proced Aesthet Dent. 2003; 15(1): 17-24". "GUREL G. Ceramic facets: from theory to practice. Quitessence Publishing 2006".) In the first place, the practitioner prepared an esthetic design that corresponds to the final shape of the tooth and its arrangement on the arch. The esthetic design is produced from a wax-up. It permits its validation by the practitioner and the patient, from the esthetic and functional plan before it is performed. It will also be used as a guide during preparation. The practitioner must then prepare the tooth while preserving a maximum of enamel (in other words, by avoiding unnecessary removal of tissue) and by providing the dental technician with a constant thickness to build the ceramic facet. In practice, the thickness of the ceramic facet must be at least 0.5 mm on the labial surface and at least 1.5 mm on the incisal edge. The difficulty consists of prepare the tooth as a minimum to obtain these thicknesses. To do so, a replica of the esthetic project is applied in the mouth. The practitioner mills roots of about 0.5 mm deep throughout the esthetic design on the surface of the teeth. After having removed the esthetic design, it suffices then to smoothen the dental surface to be prepared without removing more dental tissue than what is necessary. An imprint is made again by using the silicone key which initially was used to produce the esthetic design. It is from this new imprint that the dental technician prepares the ceramic fact on measure. To obtain an optimal result, this technique, namely removal of the dental tissue and of making the imprint that follows, can only take place by experienced practitioners.

SUMMARY

An objective of the invention is to automate this technique, so that it can be implemented by a less experienced practitioner.

Another objective of the invention is to propose a device or equipment that enables minimizing dental tissue removal.

Another objective of the invention is to propose a device or equipment that permits improving the accuracy of making the imprint after preparing the tooth.

To do so, a robotic dental device has been developed by the inventors.

Robotic dental equipment or devices are well-known to the expert in the field. As such, for instance, through patent document WO 94/03120 (BECKETT CORP LTD), a dentistry assembly comprising a cutting tool associated with a splint. The dentist can position the cutting tool at a desired location, with respect to a patient's tooth. The tool remains always in a controlled fashion, in the desired position so that an extremely precise recess or cavity can be made in the tooth even if the patient moves his head.

This type of device does not allow complex drilling and is not adapted for preparing a tooth for performing a facet according to the technique defined before.

Also, through patent document EP 0.345.975 (LORAN), there is a device comprising a cutting tool moved along a predetermined trajectory. The manual work of the dentist is previously done on a model; the device is secured to said model in a fixed position by means of a splint. The displacement motors of the tool are called upon in response to the manipulations by the dentist of control crayons so as to displace said tool along the trajectories required to obtain the desired configuration of the tooth. Signals corresponding to the tool movements are transmitted to a computer. When tooling is completed on the model, restoration is prepared from this model and the patient is called back. Now, the device is attached to the patient's jaw so that it is precisely in the same relative position as the one that it occupied with respect to the model. Then, the computer sends signals to the appropriate control motors for repeating the movement of the tool, in accordance with the correct sequence previously recorded, so as to reproduce the tooling operations previously made on the model.

This device can be adapted to prepare a tooth for performing a facet according to the previously defined technique. However, if the dentist's manual work initially performed on the model is not of good quality, the device will reproduce all flaws inside the mouth. Consequently, the objective pursued by this invention cannot be achieved by this device.

Patent document US 2004/015175 (COSMAN) concerns a dental imprint stereotactic localizer system which permits to induce non-invasive images of tomographic sections by computer of a patient's anatomy. This type of device is not adapted for the automated preparation of teeth for achieving a partial or peripheral dental restoration.

The solution proposed by the invention is an intraoral device for the automated preparation of the teeth for achieving partial or peripheral restorations, comprising:

A splint suitable for positioning itself in a patient's mouth, with said splint comprising means for keeping it in position in the mouth, At least one mobile cutting tool associated with said splint, An electronic management unit for guiding or controlling said cutting tool, This device includes the following remarkable features:

Said cutting tool is configured to cut at least the labial surface of the tooth to be prepared with said tool being mounted on a mobile carriage that moves on a rail attached to the splint, opposite the labial surface of the tooth to be prepared and with said rail having a curvature adapted to the patient's dentures, Said splint includes at least a 3D digitizing tool so as to digitize at least the labial surface of said tooth to be prepared, with said digitizing tool connected to a management unit so that the digitized data may transit to said management unit, Said management unit is configured to guide or control the movement of said cutting tool according to the digitized data.

Thanks to this device, it is now possible to automate tooth cutting so that any practitioner, irrespective of his level of experience, can easily implement the technique developed by Dr. GUREL. Indeed, the cutting tool is now solely controlled on the basis of scanned data by the digitizing tool (in other words, on the basis of the morphology of the labial surface of the tooth), and no longer on the basis of the technical skill and dexterity of the practitioner. Drilling can as such be achieved very accurately. The same is true for making imprints which is much more accurate than the one performed from the silicone key that was initially used to produce the esthetic design. Optimizing the removal of dental tissue combined with the accurate digitizing of the tooth, enables obtaining a facet that has the minimum thickness required for its manufacture.

Other remarkable features of the intraoral device covered by the invention are listed below; each of these features can be considered by itself or in combination, irrespective of the remarkable features defined above:

The cutting tool is preferably a rotating drilling tool mounted on the mobile carriage.

The digitizing tool is preferably mounted on a mobile carriage; said carriage moves on a rail attached to the splint opposite the labial surface of the tooth to be prepared; said rail has a curvature suitable to the patient dentition.

The cutting tool is preferably removable on a counter-angle including a ball joint or pivot link that offers an angular displacement with respect to the tool.

In a variant of the embodiment, the cutting tool is a dental laser mounted on the mobile carriage.

The splint can be associated with another mobile cutting tool with said tool being configured to cut at least the incisal edge of the tooth to be prepared; said splint comprise another 3D digitizing tools arranged so as to digitize at least the incisal edge of the tooth to be prepared with said other digitizing tool connected to the management unit so that the digitized data may be transited to said management unit; the latter is configured to guide or control the movement of said other cutting tool on the basis of said digitized data.

This other cutting tool is preferably a rotating drilling device mounted on a mobile carriage with said carriage moving on a rail attached to the splint opposite the incisal edge of the tooth to be prepared and said rail having a curvature suitable for the patient's dentition.

The other digitizing tool is preferably mounted on a mobile carriage with said carriage moving on a rail attached to the splint opposite the occlusal edge of the tooth to be prepared; with said rail having a curvature suitable for the patient's dentition.

In an embodiment variant, the other cutting tool is a dental laser mounted on a mobile carriage with said carriage moving on a rail attached to the splint opposite the labial surface of the tooth to be prepared and said rail having a curvature suitable for the patient's dentition.

Another aspect of the invention concerns a system comprising the device according to one of the prior features and a tooling center comprising tools to automatically machine a dental facet, with the management unit of said device being configured to guide or control the movement of said machines tools on the basis of the digitized data by the 3D digitizing tool; said data are those of at least the labial surface of the tooth to be prepared and that of said labial surface once said tooth is prepared.

Yet another aspect of the invention involves a splint suitable for positioning inside a patient's mouth; said splint comprises means for maintaining it in position inside the mouth, with at least a mobile cutting tool associated with said splint; said tool is configured to cut at least the labial surface of the tooth to be prepared, with said tool being mounted on a mobile carriage that moves on a rail attached to the splint, opposite the labial surface of the tooth to be prepared, with said rail having a curvature suitable for the patient's dentition and with said splint comprising also at least a 3D digitizing tool arranged so as to digitize at least the labial surface of said tooth to be prepared.

Yet another aspect of the invention involves the process for guiding or controlling a mobile cutting tool associated with a splint suitable for positioning itself in a patient's mouth with said tool being configured to cut at least the labial surface of a tooth to be prepared; said process consists of:

Positioning said splint in the patient's mouth and keeping it in place;

3D digitizing at least the labial surface of said tooth to be prepared,

Guiding or controlling the movement of said cutting tool on the basis of the digitized data.

Yet another aspect of the invention involves a manufacturing technique of a dental facet consisting of:

Preparing an esthetic design corresponding to the final shape of the tooth and its arrangement on the arch.

Applying the esthetic design to the patient's tooth to be prepared,

Placing the device covered by the invention in the patient's mouth,

Launching the digitizing or scanning of the esthetic design in the mouth,

Launching the cutting of at least the labial surface of the tooth to be prepared on a predefined and constant depth with respect to the outside surface of the esthetic design in the mouth, Launching the digitizing or scanning of the prepared tooth, Transmitting to a machining center the digitized or scanned data of the prepared tooth and those of the esthetic design in the mouth, Manufacturing the facet on the basis of the digitized data received by the machining center.

DESCRIPTION OF THE FIGURES

Other advantages and characteristics of the invention shall become clearer when reading the description of a preferred mode of embodiment that follows, referenced against the attached drawings, prepared as indicative and non-limiting examples, where:

FIG. 6 shows the arrangement of a device according to the invention with respect to a prepared tooth with the 3D digitizing or scanning tools arranged opposite said tooth, FIG. 7 shows a schematic view of the ceramic facet to be glued onto the prepared tooth;

DETAILED DESCRIPTION

Figure 1:
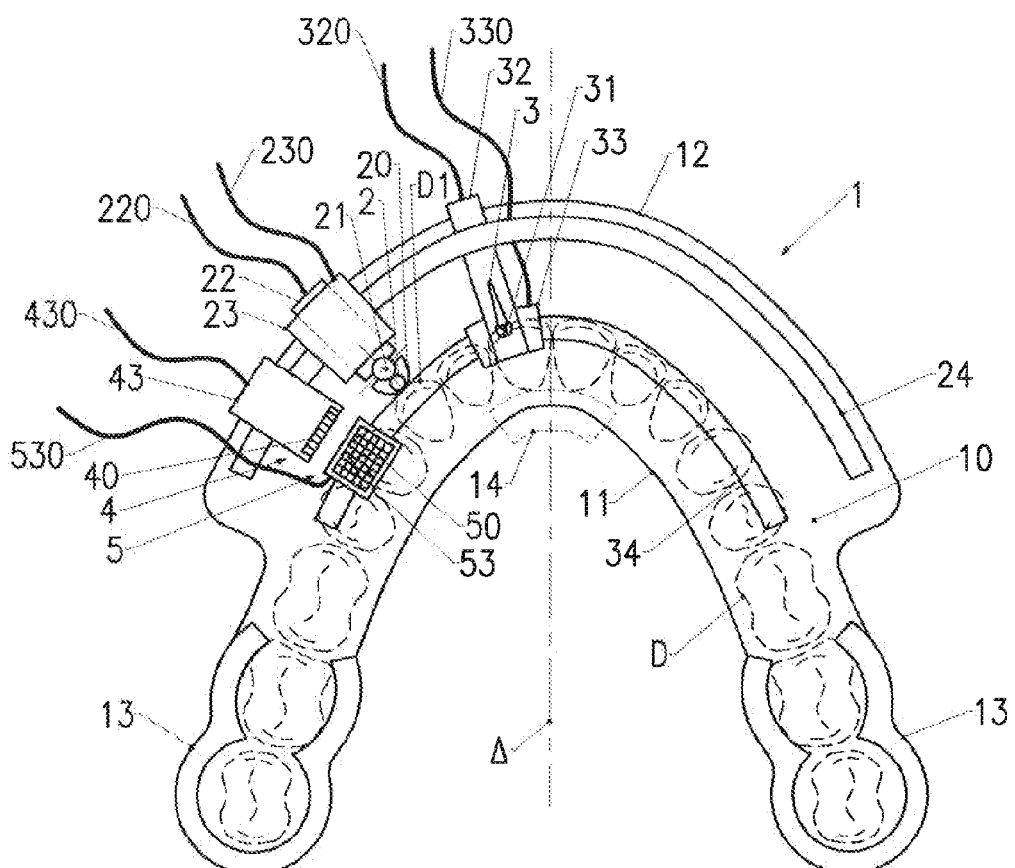
FIG. 1 shows schematically a device according to the invention seen from above.
Figure 2:
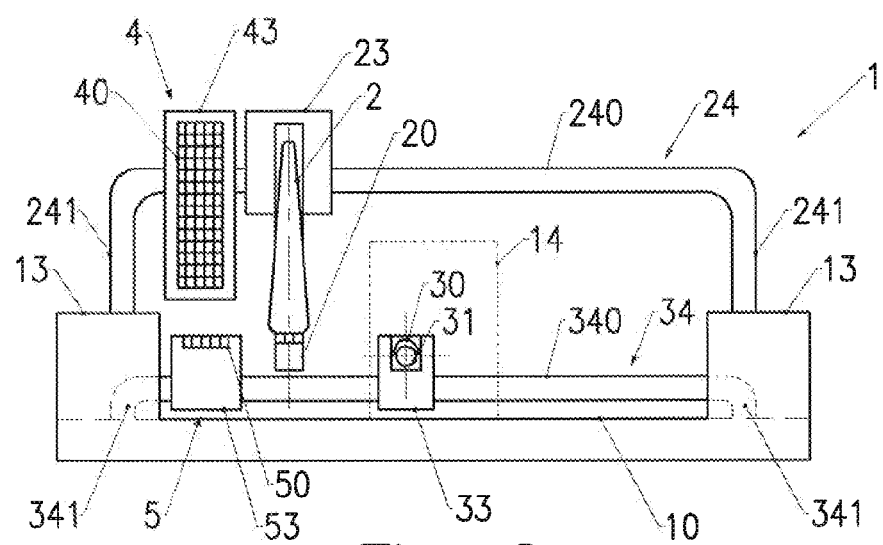
FIG. 2 shows schematically a device according to the invention seen from behind.

Referring to FIGS. 1 and 2, the device covered by the invention includes a splint 1 suitable for positioning in a patient's mouth. This splint 1 has a general "U" or "V" shape and shows a symmetrical axis with respect to the A median plane of the patient. It can be obtained by plastic molding or thermal forming. It includes a bite area 10 formed so as to adapt to the general curvature of the patient's dentition D. The bite area 10 shows an occlusion area arranged to come into contact with dentition D when it is inserted in the patient's mouth, a palatal edge 11 on a side close to the throat and a labial edge 12 on another side close to the lips.

To maintain splint 1 in position in the patient's mouth, dental clamps 13 incorporated in said splint are foreseen. These clamps 13 are arranged at the molar sectors of the occlusion area. They are secured onto the molars of the dental arch to which belongs the tooth to be prepared D1. To avoid the rocking of the labial edge 12 of splint 1, it may be beneficial to provide a silicone element arranged in the middle of the palatal edge 11 and configured to rest on the lingual face of the central incisors of the arch to which belongs the tooth to be prepared. One might also provide for another dental clamp incorporated in the splint 1 and configured to be attached on the central incisors. Other means to keep splint 1 in position inside the patient's mouth may be used. The splint 1 can, for example, include attachment areas to be filled with glue or of a hardening plastic substance.

Figure 4:
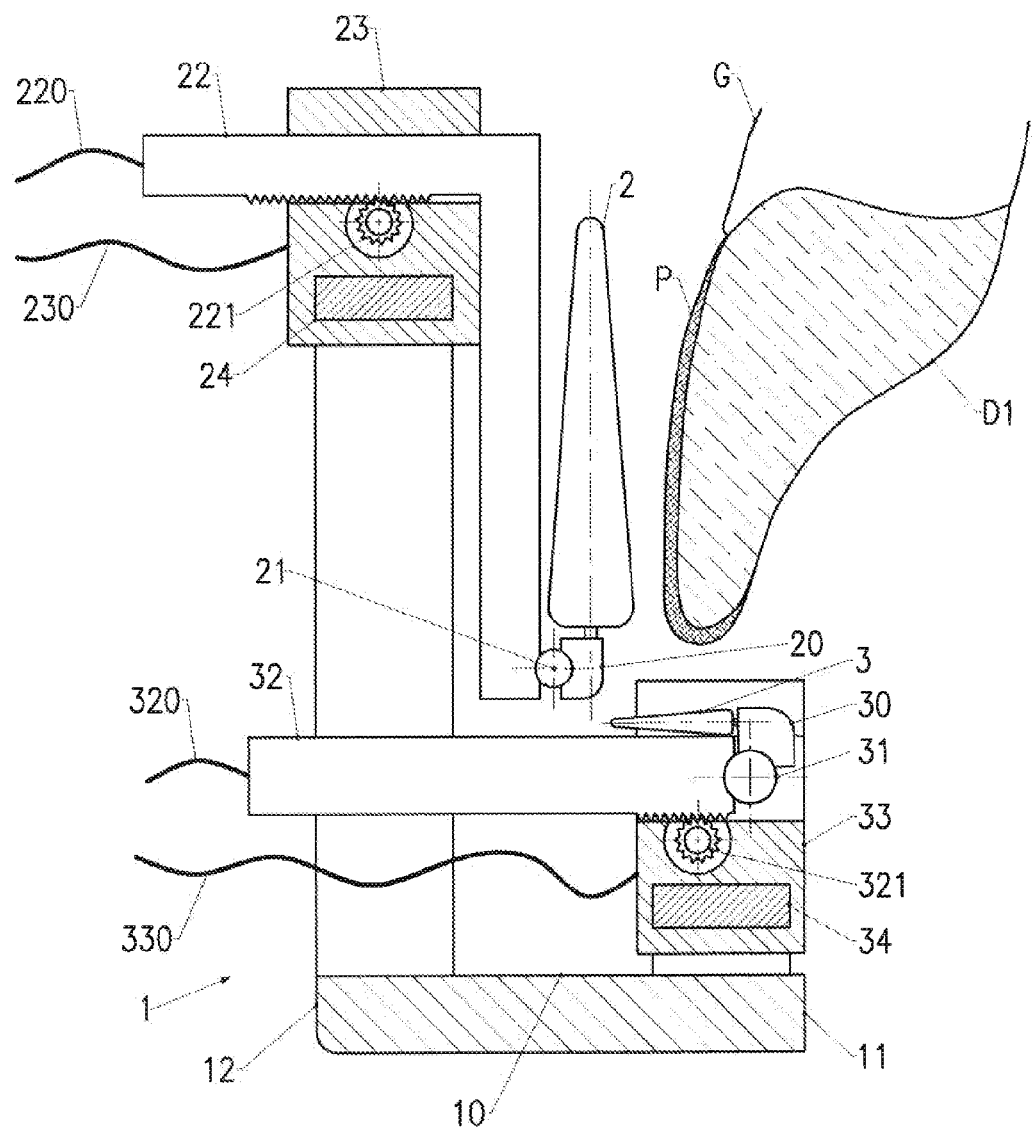
FIG. 4 shows the arrangement of a device according to the invention with respect to the prepared tooth, with the cutting tools arranged opposite said tooth covered by the esthetic design.

The splint 1 is associated with at least a mobile cutting tool 2 configured to cut at least the labial surface of the tooth to be prepared. Referring to FIGS. 2 and 4, preferably this would be a rotating cutting tool of the diamond bur type that can present a normal grain size (to reduce the dental volume) or a low grain size (polishing the preparation) (other models selected by the specialist in the field may be used) mounted in a removable fashion on an counter-angle 20, like the classic drilling tools of dentistry. The length of the active part of this bur is considerably equal, preferably slightly greater, than the average length of a tooth. The rotation axis of the tool 2 is initially considerably vertical. The cutting tool 2 is arranged on the splint 1 so that it can correctly reach and prepare the labial surface of the tooth to be prepared among which its cervical limits.

Figure 5:
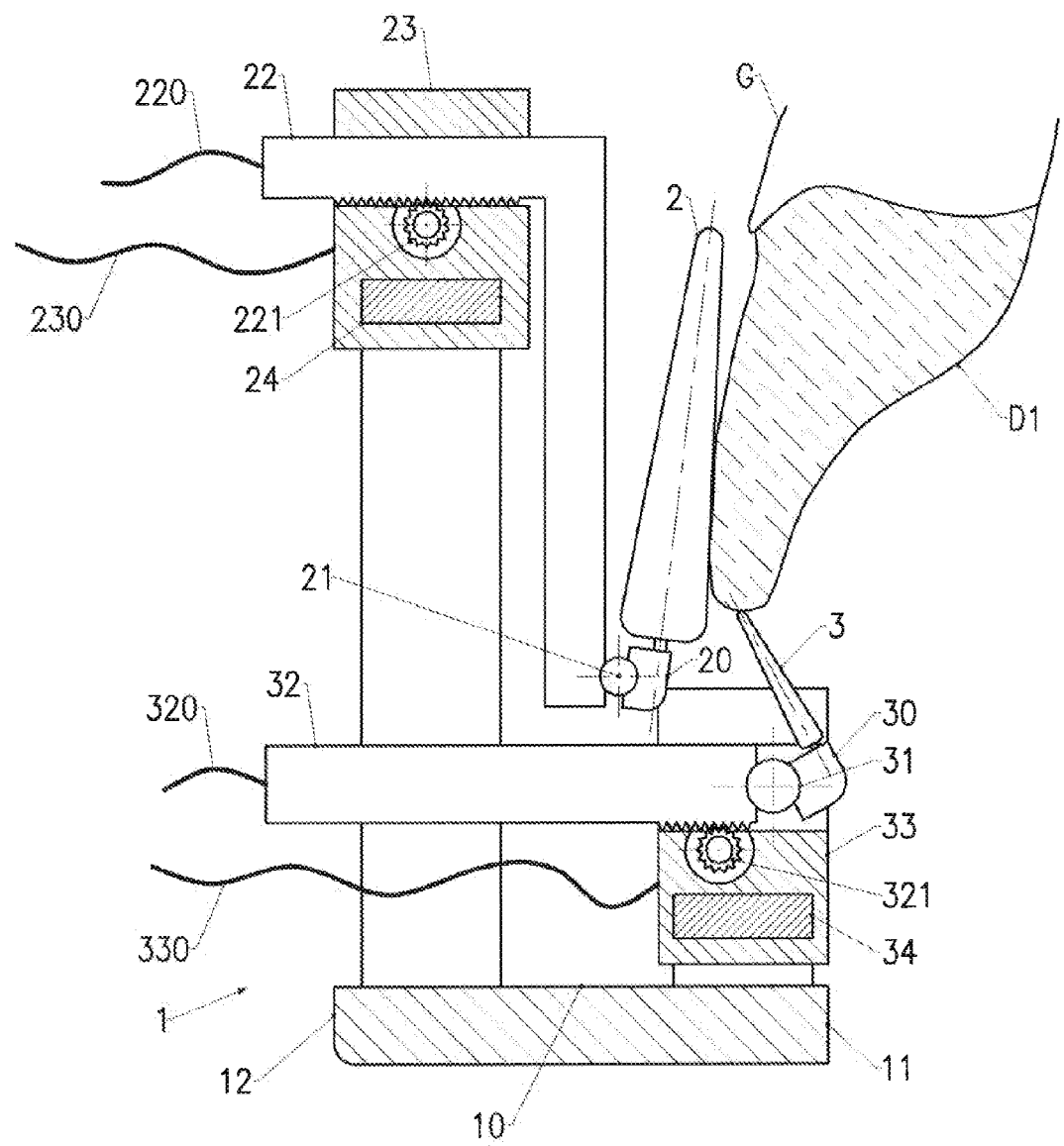
FIG. 5 shows the device of FIG. 2 with the cutting tools in operation.

The counter-angle 20 includes a ball joint or pivot link 21. This link 21 offers an angular displacement with respect to the tool 2 (FIG. 5). A first motor (not shown) associated with the link 21 permits adjusting the inclination of the counter-angle 20 and consequently the angle of tool 2. This first motor includes for instance an electric motor associated with a pinion/toothed wheel system which permits to modify the inclination of counter-angle 20. Link 21 is incorporated in a handle 22 inside of which are housed all components that make the cutting tool 2 work and the first motor. A water and/or air spray may be provided to cool the working area. Indeed, the handle 22 includes an electric, hydraulic and/or pneumatic connection 220, provided for that purpose.

The handle 22 is mounted on a mobile carriage 23. The latter is described in greater detail later in the description. In practice, the handle 22 is mounted sliding in the mobile carriage 23, a second motor 221 permits to make said handle slide automatically forward or backward, in other words towards the palatal edge 11 or towards the labial edge 12. This second motor 221 includes for instance an electric motor associated with a pinion/rack system enabling the movement of handle 22.

The mobile carriage 23 moves about on a rail 24 attached to the splint 1. The rail 24 is preferably made of stainless steel. It is arranged opposite the labial surface of tooth D1 to be prepared; its curvature is suitable for the patient's dentition D. Referring more in particular to FIGS. 1 and 2, the rail 24 includes a curved portion 240, considerable vertical, and for which the extremities end in two jambs 241 attached at the labial edge 12 of the bite area 10 of the splint 1. The curved portion 240 is offset by a few millimeters of the bite area 10 so that the mobile carriage 23 is located considerably at the level of gum G of the patient (FIG. 4). A third motor (not shown) allows the automatic movement of the mobile carriage 23 on the rail 24. This third motor may consist of an electric motor associated with a pinion/rack system that permits moving the mobile carriage 23. The latter includes an electric connection 230 that permits the operation of the second and third motor.

The cutting tool 2 thus comprising at least three degrees of movement: a first degree corresponding to the inclination of counter-angle 20, a second degree corresponding to the movement of the handle 22 in the carriage 23 and a third degree corresponding to the movement of said carriage on the rail 24. For that reason, the terms "articulated tool" or "mobile tool" are used. Other movements may obviously be provided. These different movements are controlled by the motors mentioned before so that tool 2 may cut at least the labial surface of tooth D1 to be prepared, irrespective of the morphology of the latter and the quantity of tissue to be removed.

For an embodiment variant not shown, cutting of the labial surface of tooth D1 to be prepared can be performed using a dental laser such as an Erbium laser, capable of treating the hard surfaces such as enamel. In this case, the cutting tool 2 is shown for instance in the form of a laser mounted on a mobile carriage 23 of the type previously described. This laser has degrees of movement enabling it to cut the labial surface of tooth D1 to be prepared irrespective of the morphology of the latter and the quantity of tissue to be removed.

According to the configuration of the facet to be performed, it may be necessary of also cutting the incisal edge of tooth D1 to be prepared. To do so, it is considered to associate splint 1 to at least another cutting tool 3 configured to cut at least the occlusal edge of tooth D1 to be prepared. Referring to FIGS. 1, 2 and 4, it is preferred to use a rotating cutting tool of the diamond bur type mounted in removable fashion on a counter-angle 30. Taking into account the small surface to cut, the length of the active part of this bur is less than that of tool 2. A round bur may be used equivalently.

Counter-angle 30 is provided with a ball or pivot joint link 31. This link 31 allows for an angular movement of the tool 3 (FIG. 5). A first motor (not shown) associated with link 31 permits to adjust the inclination of counter-angle 30 and consequently of the tool 3 angle. This first motor includes for instance an electric motor associated with a pinion/toothed wheel system that permits modifying the inclination of the counter-angle 30. The link 31 is part of a handle 32 inside of which are housed all electric, hydraulic and/or pneumatic connections 320 which make the cutting tool 3 and the first motor operate. The handle 32 includes an electric, hydraulic and/or [ . . . ] foreseen for this purpose. A water and/or air spray may be foreseen to cool down the work area.

The handle 32 is mounted on a mobile carriage 33. In practice, the handle 32 is mounted sliding in the mobile carriage 33, a second motor 321 permits the automatic sliding of said handle forward or backward, in other words towards the palatal edge 11 or towards the labial edge 12. This second motor 221 includes for instance an electric motor associated with a pinion/rack system that lets the handle 32 move about.

The mobile carriage 33 moves about on a rail 34 attached to the splint 1. The rail 34 is preferably made of stainless steel. It is arranged opposite the incisal edge of tooth D1 to be prepared, its curvature is suitable for the patient's dentition D. Referring in particular to FIGS. 1 and 2, the rail 34 includes a curved portion 340 that is considerably vertical and for which the extremities end in two jambs 341 secured considerably in the middle of the bite area 10 of the splint 1. Curved portion 340 is located under the incisal edge of tooth D1 to be prepared (FIG. 4). Consequently, it is lower than the curved portion 240 of the rail 24 and closer to palatal edge 11. A third motor (not shown) permits to move automatically the mobile carriage 33 on the rail 34. This third motor may consist of an electric motor associated with a pinion/rack system that permits moving the mobile carriage 33. The latter includes an electric connection 330 that lets operate the second and third motor.

Consequently, the other cutting tool 3 also includes at least three degrees of displacement: a first degree corresponding to the inclination of counter-angle 30, a second degree corresponding to the movement of the handle 32 in the carriage 33 and a third degree corresponding to the movement of said carriage on the rail 34. Other movements may obviously be provided. These different movements are controlled by the motors mentioned before so that tool 3 may cut at least the incisal edge of tooth D1 to be prepared, irrespective of the morphology of the latter and the quantity of tissue to be removed.

For an embodiment variant not shown, cutting of the incisal edge of tooth D1 to be prepared can be performed using a dental laser such as an Erbium laser capable of treating the hard tissues such as enamel. In this case, the cutting tool 3 is shown for instance in the form of a laser mounted on a mobile carriage 33 of the type previously described. This laser has degrees of displacement enabling it to cut the incisal edge of tooth D1 to be prepared irrespective of the morphology of the latter and the quantity of tissue to be removed. It is to be noted that the cutting of the labial surface and the incisal edge of tooth D1 to be prepared, may be done using a single dental laser having degrees of displacement enabling such cutting.

Figure 9:
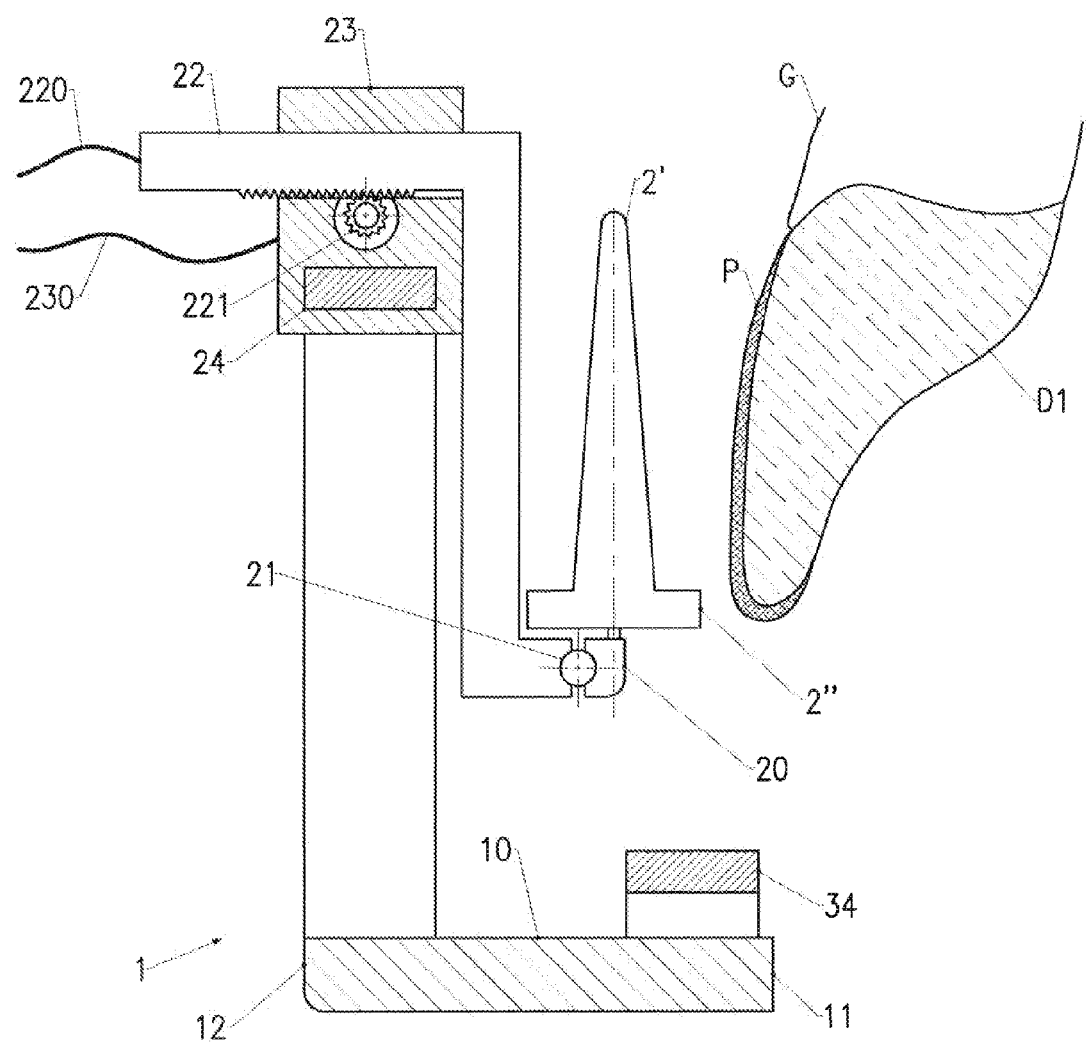
FIG. 9 shows the arrangement of a device according to the invention with respect to the tooth to be prepared with a single tool permitting to cut the labial surface and the incisal edge of the tooth to be prepared.

According to yet another variant of embodiment shown on FIG. 9, a single rotating cutting tool 2', 2" permits preparing the labial surface and the incisal edge of tooth D1. Management unit 6 consequently manages now only the movement of a single tool. This tool is similar to tool 2 described in reference to FIGS. 4 and 5, and it includes the same number of degrees of displacement. It is secured in a removable fashion on the counter-angle 20 previously described. This tool includes a first portion 2' of the diamond bur type. The low extremity of this first portion is provided with a second diamond cylindrical portion 2". This second portion 2" is positioned opposite the incisal edge of tooth D1 to be prepared. By moving the handle 22, the second portion 2" is consequently in a position to remove tissue at the incisal edge of tooth D1.

Referring to FIG. 1, the presence of the rails 24, 34 and of the different elements they support, the labial edge 12 is moved forward, generally exceeding the patient's mouth.

Figure 8:
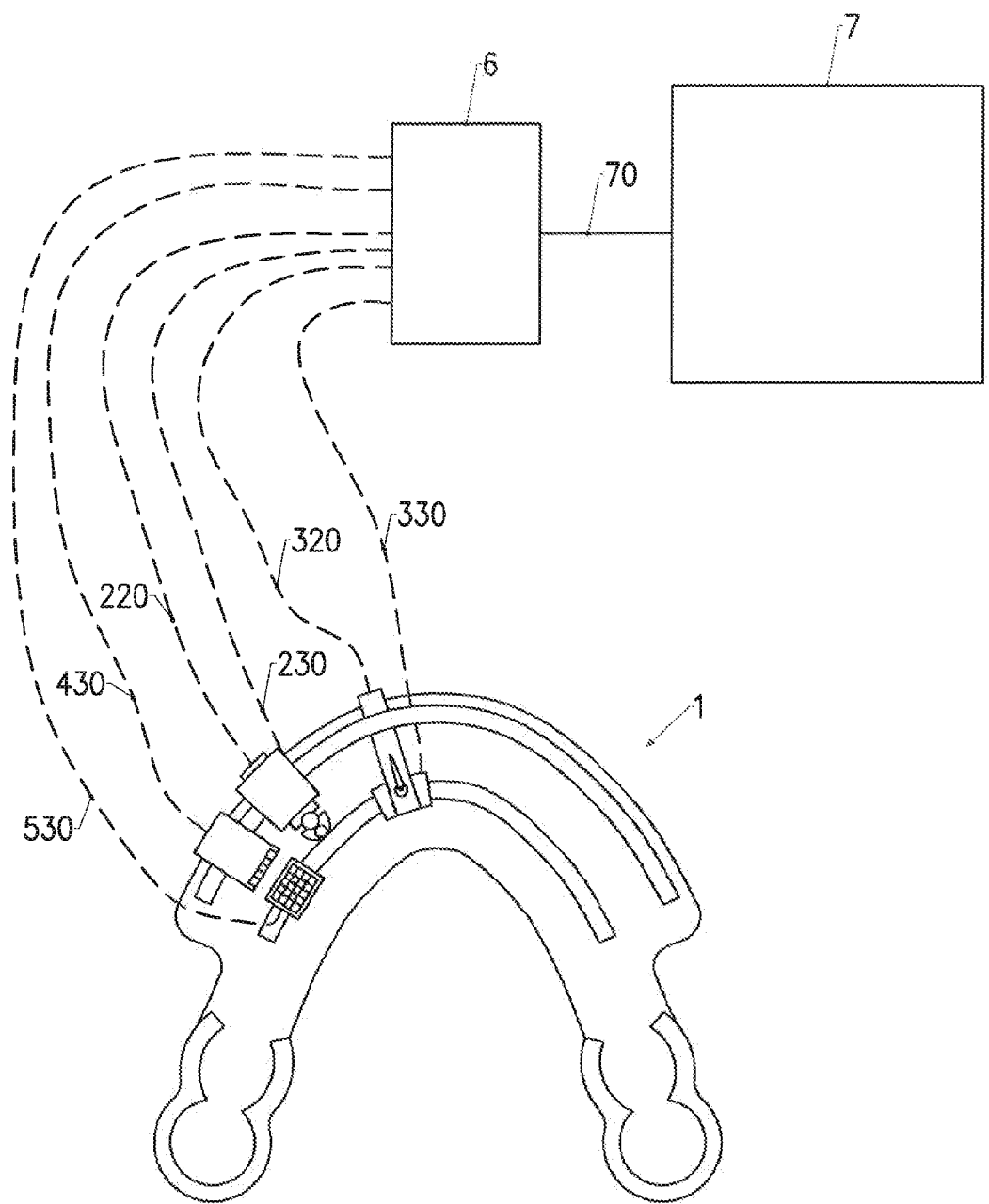
FIG. 8 shows a device according to the invention.

Referring to FIG. 8, connections 220, 230, 320 and 330 are tied to the electronic management unit 6 by a wire link or wireless of the Wifi-type, Internet or Bluetooth. In practice, the electronic management unit 6 presents itself in the form of a computer equipped with a processor, configured to execute one or several programs, subprograms, micro programs or any other equivalent types of software for which the instructions permit to manage the inclination of counter-angles 20 and 30, the movement of the handles 22 and 32, the movement of the carriages 23 and 33, respectively on the rails 24 and 34, the rotation of tools 2 and 3 or their shutdown. The electronic management unit 6 consequently permits guiding or controlling cutting tools 2 and 3.

Figure 3:
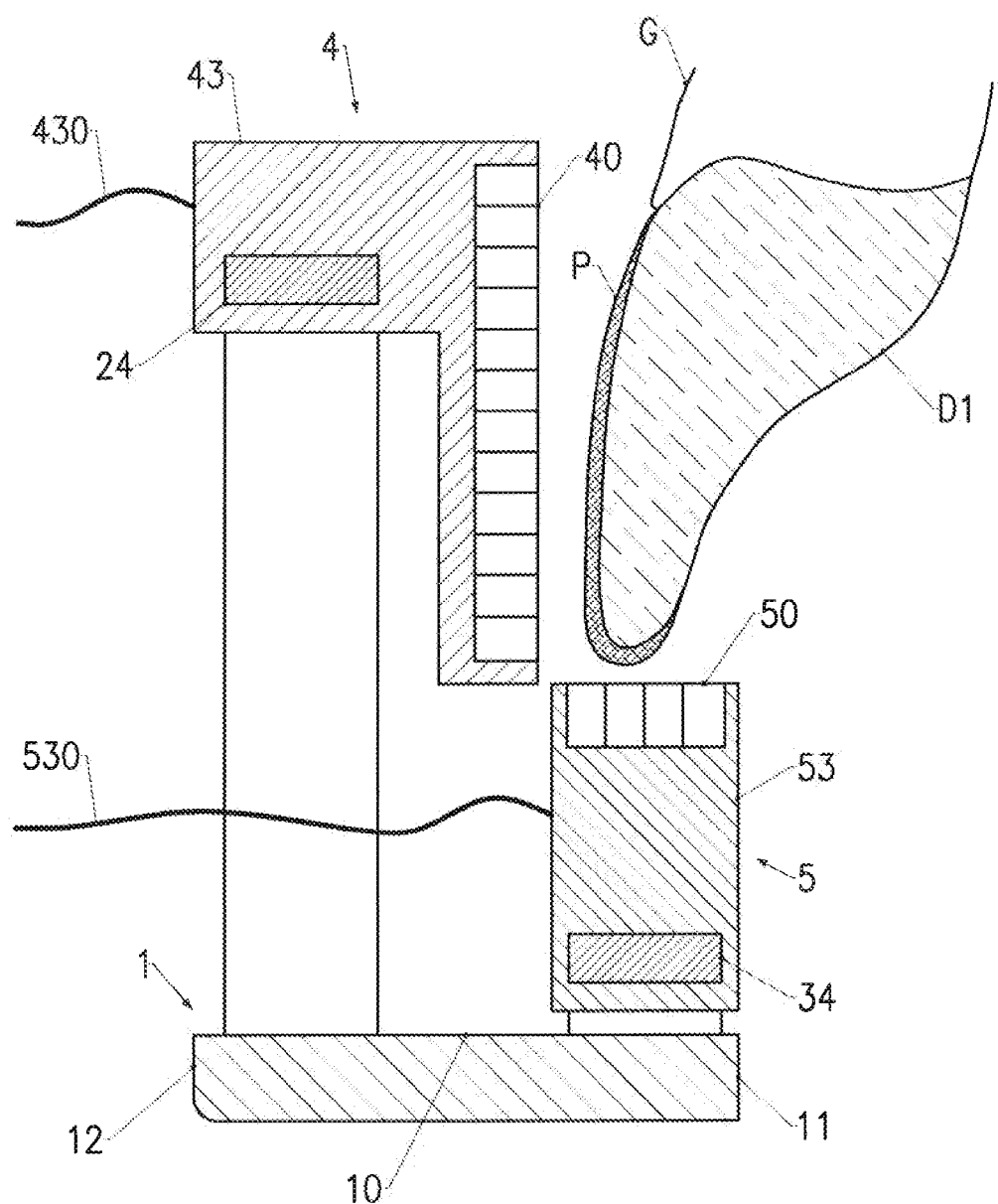
FIG. 3 shows schematically a device according to the invention with respect to the tooth to be prepared with the 3D digitizing or scanning tools arranged opposite said tooth covered by the esthetic design.

According to the invention, the splint 1 includes at least a tool 4 for 3D digitizing. This tool consists preferably of a camera capable of capturing images in 3 dimensions. Such digitizing tools are for instance described in patent documents US 2005/023781 (KNIGHTON) or US 2004/0155975 (HART) or marketed by the 3M® company under the name "intraoral camera Lava C.O.S.". Referring to FIG. 3, the digitizing tool 4 is arranged on the splint 1 so as to digitize at least the labial surface of tooth D1 to be prepared, in other words, covered with esthetic design P. For that and as shown in FIGS. 1 to 3, the tool 4 includes sensors 40 arranged vertically, considerably over the average length and average width of a tooth.

The digitizing tool 4 is preferably mounted on a mobile carriage 43. For reasons of compactness, the mobile carriage 43 moves preferably on the rail 24 previously described. The rail 24 consequently supports not only the carriage 23 associated with the cutting tool 2, but also the carriage 43 associated with the digitizing tool 4. However, it is conceivable to foresee another similar rail attached to the splint opposite the labial surface of tooth D1 to be prepared with said rail having a curvature suitable for the patient's dentition. A motor (not shown) enables the automatic movement of the mobile carriage 43 on the rail 24. This motor may consist of an electric motor associated with a pinion/rack system enabling the movement of the mobile carriage 43. The latter includes an electric connection 430 that permits operation of the digitizing tool 4.

The splint 1 may include another 3D digitizing tool 5 of the type described previously. However, referring to FIG. 3, this other digitizing tool 5 is arranged on the splint 5 so as to digitize at least the incisal edge of tooth D1 to be prepared. For that, and as shown on FIGS. 1 to 3, the other tool 5 includes sensors 50 arranged horizontally, considerably over all of the average width and average thickness of a tooth.

The other digitizing tool 5 is preferably mounted on a mobile carriage 53. For reasons of compactness, this mobile carriage 53 moves preferably on the rail 34 previously described. The rail 34 consequently supports not only the carriage 33 associated with the cutting tool 3, but also the carriage 53 associated with the digitizing tool 5. However, it is conceivable to foresee another similar rail attached to the splint opposite the incisal edge of tooth D1 to be prepared, with said rail having a curvature suitable for the patient's dentition. A motor (not shown) permits the automatic movement of the mobile carriage 53 on the rail 34. The mobile carriage 53 includes an electric connection 530 that lets the digitizing tool 5 operate.

Referring to FIG. 8, the connections 430 and 530 are linked to the electronic management unit 6 by a wire or wireless link of the Wifi-type, internet or Bluetooth. The data digitized by the tools 4, 5 can as such be transmitted to the management unit 6. In practice, the electronic management unit 6 incorporates one or several programs, subprograms, micro programs or all other equivalent types of software, for which the instructions permit to manage the movement of the carriages 43 and 53 respectively on the rails 24 and 34 as well as the activation/deactivation of the tools 4, 5. The latter are consequently guided or controlled by the electronic management unit 6.

According to another remarkable feature of the invention, the management unit 6 is configured to guide or control at least the movement of the first cutting tool 2 on the basis of the data digitized by the first digitizing tool 4. In practice, the management unit 6 also guides or controls the movement of the second cutting tool 3 on the basis of the data digitized by the second digitizing unit 5. And more in general, the management tool 6 guides or controls the movement of the cutting tools 2, 3 on the basis of the data digitized by the digitizing tools 4, 5 and consequently on the basis of the morphology of the tooth to be prepared. The management unit 6 can also guide or control automatically the movement of the cutting tools 2, 3 so that the latter cut homogenously the tooth D1 to be prepared (e.g. covered by esthetic design P), on a predefined and constant depth: for instance 0.2 mm to 0.5 mm (depth d1, FIG. 6) with respect to the digitized labial surface and 0 mm to 1.5 mm (depth d2, FIG. 6) with respect to the digitized incisal edge. The practitioner is consequently certain to obtain a micro-abrasion of the tooth where only the quantity of dental tissue necessary and sufficient for making the facet is removed. The depth of preparation of the labial surface and/or of the incisal edge is chosen by the practitioner on the basis of the clinical situation (for instance, in case of a tooth with discolorations, the thickness required for the facet will not be 0.5 mm as generally suggested, but rather 0.8 mm to 1 mm, so that said facet may hide the discoloration). In practice, the management unit 6 suggests to the practitioner to define, through an interface on the screen, the penetration depth of the preparation tools.

In short, using the cutting tool 2 (respectively cutting tool 3) is done by positioning the splint 1 in advance in the patient's mouth and by keeping it in position, then, by 3D digitizing at least the labial surface (respectively the incisal edge) of tooth D1 to be prepared. Guiding or controlling the movement of the tool is then done on the basis of the digitized data.

For an embodiment variant, one might associate each cutting tool 2, 3 to a probe configured to measure the depression of said tool in the labial surface and/or in the incisal edge of tooth D1 to be prepared. This probe is connected to a management unit 6 so that the data regarding the measured depth may be passed on to the management unit. The latter can now automatically guide or control the movement of each cutting tool 2, 3 so that the latter cut homogenously the tooth to be prepared D1 covered with the esthetic design, on a predefined depth controlled by the probes.

Referring to FIG. 8, the device covered by the invention can be associated with a machining center 7 which is located at the practitioner's office or in another location. The machine center 7 consists for instance of a CNC digital drill CNC with 4 axes for dental prostheses, marketed under the reference CHARLYDENTAL® 4× by the CHARLYROBOT®COMPANY. This type of machining center is well known to the expert in the field and includes tools suitable to machine automatically a dental facet, such as ceramic or resin facets. The machining center 7 is linked to the management unit 6 by a link 70, such as a wire or wireless link of the Wifi-type, Internet or Bluetooth so that said unit may guide or control the movement of the machining tools of said center on the basis of the digitized data by digital tool 4 and/or 5. These digitized data are those of at least the labial surface of tooth D1 to be prepared (e.g. covered by esthetic design P) and that of said labial surface once that said tooth is prepared (e.g. after cutting). These digitized data can of course include those for the incisal edge before and after cutting. Indeed, once that tooth D1 is cut, the latter is again digitized by the digitizing tools 4, 5 (FIG. 6). Referring to FIG. 7, the shape and dimensions of facet F are deduced by comparing the image of tooth D1 to be prepared (e.g. covered by the esthetic design P) with the image of said prepared tooth (e.g. after cutting). Management unit 6 can also select the type of ceramic studs to be machined (translucent or opaque) on the basis of the initial clinical situation and of the esthetic design.

In summary, the invention enables the implementation of a new manufacturing technique of a dental facet consisting of:

Placing the device covered by the invention in the patient's mouth and launching the digitizing of the mouth; once this initial digitizing is done, the device can be removed from the patient's mouth, Preparing an esthetic design corresponding to the final shape of the tooth and its arrangement on the arch, Applying the esthetic design on the tooth to be prepared for the patient, Placing the device covered by the invention in the patient's mouth, Launching the digitizing of the esthetic design in the mouth: FIG. 1, the digitizing tool or tools 4, 5 are moved on their respective rail 24, 34 so that they are positioned opposite tooth D1 to be prepared, Launching the cutting of at least the labial surface and possibly the incisal edge of the tooth to be prepared, at a predefined and constant depth with respect to the outside surface of the esthetic design in the mouth: FIGS. 4 and 5, the digitizing tool or tools 4, 5 are removed from tooth D1 to be prepared to leave space for cutting tools 2, 3; the latter are moved on their respective rail 24, 34 so as to be positioned opposite said tooth, Launching the digitizing of the prepared tooth: FIG. 6, cutting tools 2,3 are removed from the prepared tooth D1 to leave space for digitizing tools 4, 5, Transmitting the digitized data of the prepared tooth and those of the esthetic design in the mouth to a machining center, Fabricating the facet on the basis of the digitized data received by the machining center.

Prior to the cutting stage, a restoration perimeter can be delimited by the practitioner. To do so, the management unit 6 is linked to a screen on which the image of the tooth to be restored is shown. Using a mouse or another pointing device, the practitioner delimits with precision the restoration perimeter on the initial image (without design) of the tooth to be restored. The management unit 6 takes into account this perimeter so that cutting tools 2, 3 remove dental tissue only inside said perimeter.

The invention claimed is:

1. Intraoral device for the automated preparation of teeth in order to perform a partial or peripheral dental restoration comprising:
   a splint suitable to be positioned in a patient's mouth, with said splint comprising clamps,
   a mobile cutting tool associated with the splint,
   an electronic management unit enabling the guidance or control of the cutting tool,
   wherein:
   the cutting tool is configured to cut at least the labial surface of the tooth to be prepared, with said cutting tool being mounted on a mobile carriage moving on a rail attached onto the splint opposite the labial surface of the tooth to be prepared, with said rail having a curvature adapted to the patient's dentition,
   the splint comprises at least a 3D digitizing tool arranged to digitize at least the labial surface of said tooth to be prepared, with said digitizing tool connected to the management unit so that the digitized data are passed on to said management unit, and
   the management unit guiding or controlling the movement of said cutting tool on the basis of the digitized data.

2. The device according to claim 1, in which the cutting tool is a rotating milling cutter.

3. The device according to claim 1, in which the digitizing tool is mounted on a mobile carriage with said carriage moving on a rail attached to the splint opposite the labial surface of the tooth to be prepared, with said rail having a curvature suitable for the patient's dentition.

4. The device according to claim 1, in which the cutting tool is mounted in a removable way at a counter-angle comprising a ball joint or pivot offering an angular displacement to such tool.

5. The device according to claim 1, in which the cutting tool is a dental laser.

6. The device according to claim 1, in which:
   the splint is associated with another mobile cutting tool which said other tool being configured to cut at least the incisal edge of the tooth to be prepared,
   said splint includes another 3D digitizing tool arranged to digitize at least the incisal edge of said tooth to be prepared, with said other digitizing tool connected to the management unit so that the digitized data can be passed on to said management tool, and
   said management tool is configured to guide or control the movement of said other cutting tool on the basis of the digitized data.

7. The device according to claim 6 in which the other mobile cutting tool is a rotating drilling device mounted on a mobile carriage with said carriage moving on a rail attached to the splint opposite the incisal edge of the tooth to be prepared, with said rail having a curvature suitable for the patient's dentition.

8. The device according to claim 6, in which the other mobile cutting tool is a dental laser mounted on a mobile carriage, with the carriage moving on a rail attached to the splint opposite the incisal edge of the tooth to be prepared, with said rail having a curvature suitable for the patient's dentition.

9. The device according to claim 6, in which the other digitizing tool is mounted on a mobile carriage with said carriage moving on a rail attached to the splint opposite the incisal edge of the tooth to be prepared, with said rail having a curvature suitable for the patient's dentition.

10. A system comprising the device according to claim 1 and a machining center comprising tools to automatically machine a dental facet, with the management unit of said device guiding or controlling the movement of said machining tools on the basis of digitized data by the 3D digitizing tool with said data being those of at least the labial surface of the tooth to be prepared and those of said labial surface once the tooth has been prepared.

11. A splint suitable for positioning itself in the mouth of a patient with said splint comprising clamps, with at least a mobile cutting tool being associated with said splint, wherein:
   the cutting tool is configured to cut at least the labial surface of the tooth to be prepared, with said tool mounted on a mobile carriage moving on a rail attached to the splint opposite the labial surface of the tooth to be prepared with said rail having a curvature suitable for the patient's dentition, and
   the splint comprising at least a 3D digitizing tool arranged to digitize at least the labial surface of said tooth to be prepared.

* * * * *

UNITED STATES PATENT AND TRADEMARK OFFICE
CERTIFICATE OF CORRECTION

PATENT NO. : 9,554,872 B2  
APPLICATION NO. : 14/398810  
DATED : January 31, 2017  
INVENTOR(S) : Stefan Koubi and Gurel Galip Page 1 of 1

It is certified that error appears in the above-identified patent and that said Letters Patent is hereby corrected as shown below:

On the Title Page

In "Applicants" (Item (71)), please replace "Stephen" with "Stefan"

In "Applicants" (Item (71)), please replace "Galip Gurel" with "Gurel Galip"

In "Inventors" (Item (72)), please replace "Stephen" with "Stefan"

In "Inventors" (Item (72)), please replace "Galip Gurel" with "Gurel Galip""

Signed and Sealed this  
Twenty-fourth Day of August, 2021

Drew Hirshfeld  
*Performing the Functions and Duties of the*  
*Under Secretary of Commerce for Intellectual Property and*  
*Director of the United States Patent and Trademark Office*